(12) United States Patent
Bouhraoua

(10) Patent No.: US 8,923,523 B2
(45) Date of Patent: Dec. 30, 2014

(54) SELECTIVE FILTERING EARPLUGS

(71) Applicant: King Fahd University of Petroleum and Minerals, Dhahran (SA)

(72) Inventor: Abdelhafid Bouhraoua, Kanata (CA)

(73) Assignee: King Fahd University of Petroleum and Minerals, Dhahran (SA)

( * ) Notice: Subject to any disclaimer, the term of this patent is extended or adjusted under 35 U.S.C. 154(b) by 281 days.

(21) Appl. No.: 13/711,486

(22) Filed: Dec. 11, 2012

(65) Prior Publication Data

US 2013/0101130 A1    Apr. 25, 2013

Related U.S. Application Data

(63) Continuation-in-part of application No. 12/659,938, filed on Mar. 25, 2010, now abandoned.

(51) Int. Cl.
*A61F 11/06* (2006.01)

(52) U.S. Cl.
USPC .............................. 381/72; 381/56; 381/328

(58) Field of Classification Search
None
See application file for complete search history.

(56) References Cited

U.S. PATENT DOCUMENTS

| | | | |
|---|---|---|---|
| 4,985,925 A | 1/1991 | Langberg et al. | |
| 5,832,094 A | 11/1998 | Le Her | |
| 6,068,079 A | 5/2000 | Hamery et al. | |
| 6,425,398 B1 | 7/2002 | Hirshfeld | |
| 6,456,199 B1 | 9/2002 | Michael | |
| 6,567,524 B1 | 5/2003 | Svean et al. | |
| 6,661,901 B1 | 12/2003 | Svean et al. | |
| 6,728,385 B2 | 4/2004 | Kvaloy et al. | |
| 6,754,359 B1 | 6/2004 | Svean et al. | |
| 6,801,629 B2 | 10/2004 | Brimhall et al. | |
| 7,120,258 B1 | 10/2006 | Burleigh et al. | |
| 7,185,734 B2 | 3/2007 | Widmer et al. | |
| 7,240,765 B2 | 7/2007 | Berg et al. | |
| 7,289,636 B2 | 10/2007 | Saunders et al. | |
| 7,369,670 B2 | 5/2008 | Haussmann | |
| 7,416,531 B2 | 8/2008 | Mohler | |
| 7,433,481 B2 | 10/2008 | Armstrong et al. | |
| 2002/0059065 A1 | 5/2002 | Rajan | |
| 2003/0096580 A1 | 5/2003 | Kaplan | |
| 2004/0257233 A1 | 12/2004 | Proebsting | |
| 2006/0042865 A1 | 3/2006 | Berg et al. | |
| 2006/0042867 A1 | 3/2006 | Haussmann et al. | |
| 2007/0290910 A1 | 12/2007 | Chen et al. | |
| 2008/0137878 A1 | 6/2008 | Killion et al. | |

FOREIGN PATENT DOCUMENTS

JP    2007166205 A    6/2007
KR    950005334       5/1995

*Primary Examiner* — Paul Huber
(74) *Attorney, Agent, or Firm* — Richard C. Litman

(57) ABSTRACT

The selective filtering earplugs allow a user to filter most external and environmental sounds, only allowing a set of pre-approved sounds to be heard by the user. The earplugs include a sound acquisition module and at least one filtering earplug. The sound acquisition module includes a microphone for receiving environmental sounds and a controller for converting the received environmental sounds to a digital signal. First memory is provided for storing the digital signal and second memory is provided for storing a database of pre-approved sound signals. The controller compares the digital signal with the database of pre-authorized sound signals. If the digital signal matches a pre-authorized sound signal of the database, then a transmitter transmits the digital signal. The filtering earplug includes a receiver for receiving the digital signal and a converter for converting the digital signal into an audio signal.

20 Claims, 5 Drawing Sheets

SELECTIVE FILTERING EARPLUGS

CROSS-REFERENCE TO RELATED APPLICATION

This application is a continuation-in-part of U.S. patent application Ser. No. 12/659,938, filed Mar. 25, 2010.

BACKGROUND OF THE INVENTION

1. Field of the Invention

The present invention relates to listening devices, and particularly to a selective filtering earplugs that allow a user to filter most external and environmental sounds, only allowing a set of approved or desired sounds to be heard by the user.

2. Description of the Related Art

In recent years, with the advent of urban living, noise pollution has become an increasingly significant problem. Loud noise is also a problem in the workplace, where high levels of machinery noise can cause damage to the ears. In fact, to protect workers, there exists in many countries legislation requiring employers to provide ear protection for their employees.

Noise pollution, while being an irritation, is also a cause of hearing loss when the ears are either subjected to a single loud noise or are repeatedly subjected to levels of noise above a safe maximum. Ear protection has traditionally taken the form of earplugs constructed of plastic, foam, silicone or wax. All of these tend to have disadvantages and are of varying effectiveness in attenuating noise. Outside of conventional concerns, such as discomfort or pressure differentials in the ears, such earplugs act to block all noise from entering the ear canals of the user. Thus, even desired noises, such as the sound of a ringing telephone or an emergency alarm, may be blocked by the ear protection.

Thus, selective filtering earplugs solving the aforementioned problems are desired.

SUMMARY OF THE INVENTION

The selective filtering earplugs allow a user to filter most external and environmental sounds, only allowing a set of approved or desired sounds to be heard by the user. For example, the user may insert a pair of selective filtering earplugs and choose to only allow the sound of a ringing telephone or the sound of an emergency siren to be transmitted into the user's ear canals. The selective filtering earplugs include a sound acquisition module and a pair of earplugs, at least one of the earplugs being a filtering earplug. The sound acquisition module includes a microphone for receiving environmental sounds and a controller for converting the received environmental sounds to a digital signal representing the received environmental sounds.

First memory is provided for storing the digital signal representing the received environmental sounds, and second memory is further provided for storing a database of pre-authorized sound signals. The controller compares the digital signal representing the received environmental sounds with the database of pre-authorized sound signals. A transmitter is further provided. If the digital signal representing the received environmental sounds matches a pre-authorized sound signal of the database, then the transmitter transmits the digital signal.

The filtering earplug includes a housing adapted for insertion into an ear canal of the user. The housing is sized and shaped to completely block out environmental noise from entering the ear canal. The housing contains a receiver for receiving the digital signal and a converter for converting the digital signal into an audio signal. A speaker is in communication with the converter to play the transmitted environmental sound for the user.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
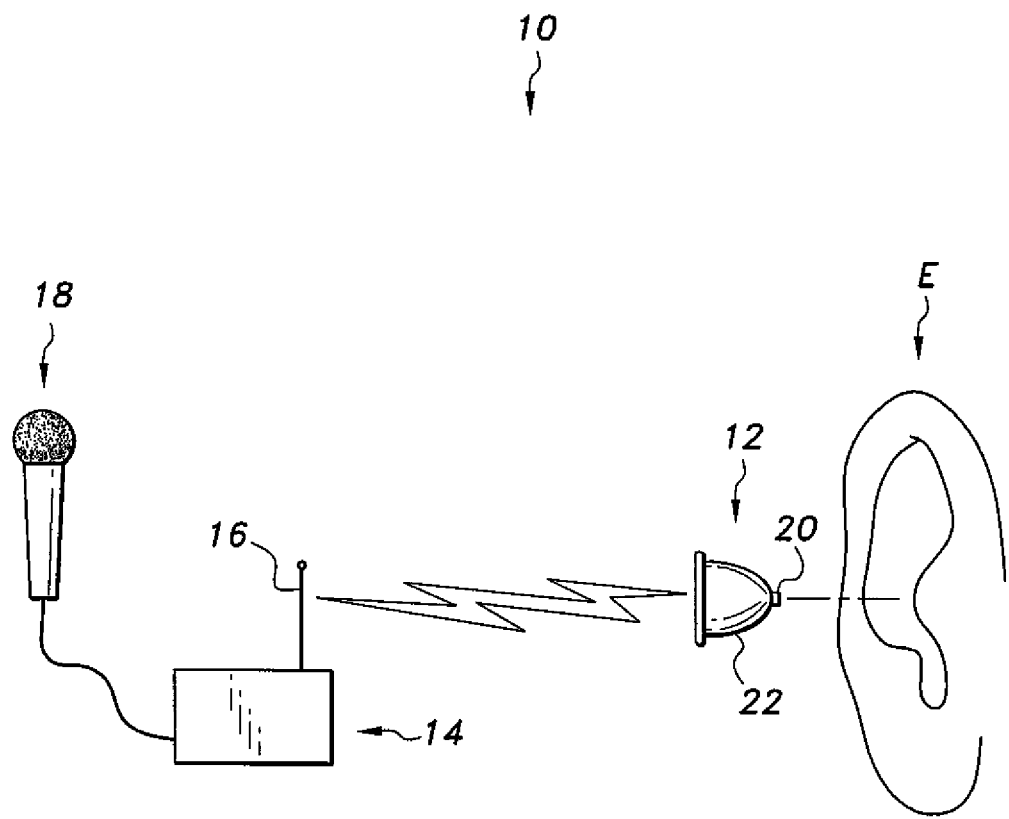
FIG. 1 is a schematic diagram showing an overview of selective filtering earplugs according to the present invention.

Referring to FIG. 1, the selective filtering earplugs 10 allow a user to filter most external and environmental sounds, only allowing a set of pre-approved or desired sounds to be heard by the user. For example, the user may insert a pair of selective filtering earplugs 12 in his or her ears E and choose to only allow the sound of a ringing telephone or the sound of an emergency siren to be transmitted into his or her ear canals. The selective filtering earplugs 10 include a sound acquisition module 14 and a pair of earplugs, at least one of the earplugs being a filtering earplug 12. The earplugs 12 are of the type that totally block external sound. At least one earplug 12 is modified to play back desired or pre-approved sounds (for monaural hearing), or both earplugs 12 may be modified to play back desired sounds (for stereo sound).

Figure 2:
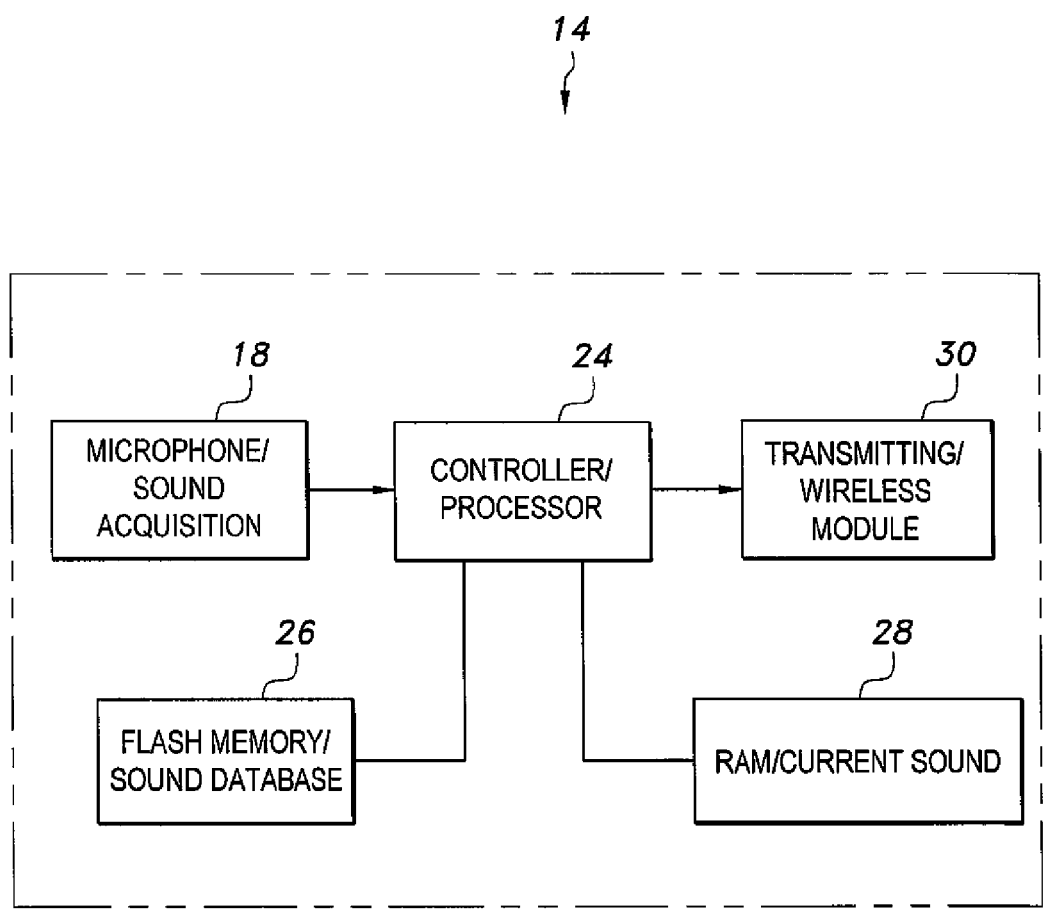
FIG. 2 is a block diagram of the control module circuits for selective filtering earplugs according to the present invention.
Figure 3:
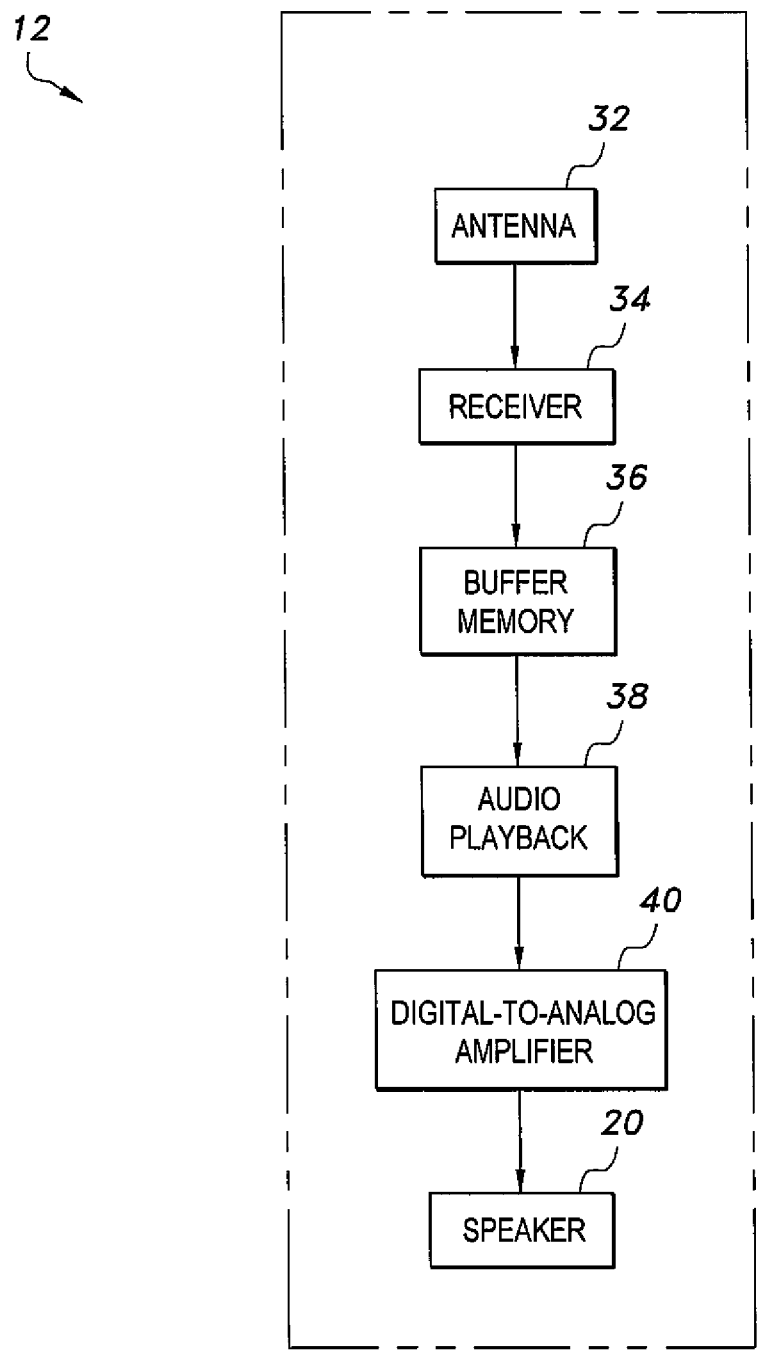
FIG. 3 is a block diagram of components of a circuit housed in the earpiece of selective filtering earplugs according to the present invention.
Figure 4:
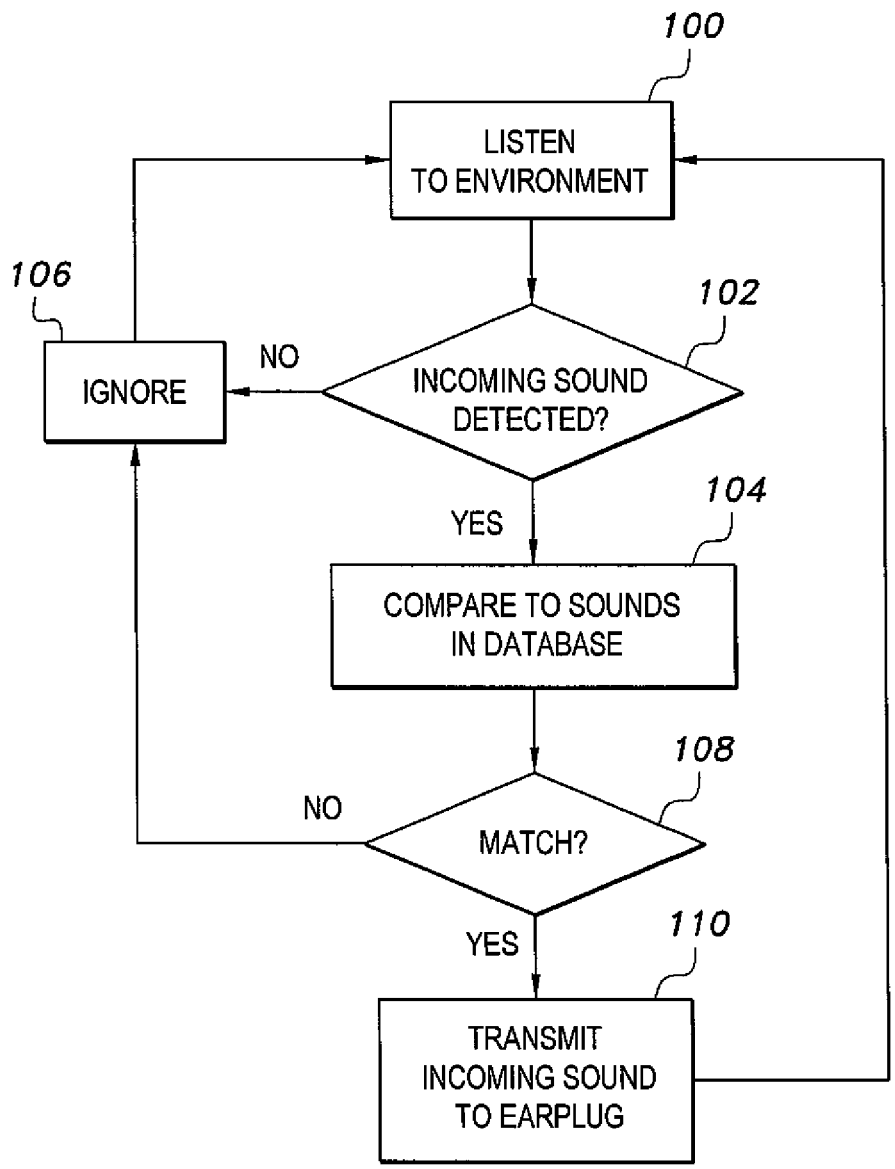
FIG. 4 is a flowchart showing the steps carried out by the circuits of selective filtering earplugs according to the present invention.

As best shown in FIG. 2, the sound acquisition module 14 includes a microphone 18 or any other suitable type of acoustic transducer for constantly receiving environmental sounds (step 100 in FIG. 4). The microphone 18 is in communication with a controller 24 such that when an incoming sound is detected (step 102), the received incoming environmental sound is converted to a digital signal (e.g., by an analog-to-digital converter) representing the received environmental sounds.

The controller 24 may be any suitable type of microcontroller, microprocessor, digital signal processor, or the like. Additionally, any suitable type of display or interface, or record and playback buttons to record and verify sounds in the database, may be provided to the user, allowing the user to program the controller 24. The controller 24 may be associated with, or incorporated into, any suitable type of computing device, for example, a personal computer.

First memory 28, such as random access memory (RAM) or the like, is provided for storing the digital signal representing the received environmental sounds, and second memory 26, e.g., flash memory, is further provided for storing a database of pre-authorized sound signals. The user selects any desired set of sounds that he or she will permit to be heard, such as the sound of a ringing telephone or emergency siren.

The user records these pre-authorized sounds with microphone 18. Controller 24 converts these pre-authorized sounds into digital signals and records them in the database of second memory 26.

The controller 24 compares the digital signal representing the received environmental sounds (stored in first memory 28) with the database of pre-authorized sound signals stored in second memory 26 (step 104 in FIG. 4) using digital signal processing algorithms. A transmitter 30, which is preferably a wireless transmitter module or assembly, is provided. If the digital signal representing the received environmental sounds matches a pre-approved sound signal in the database 108, then the transmitter 30 transmits the digital signal (step 110). It should be understood that any suitable type of transmitter may be utilized. Preferably a wireless antenna 16 is in communication with transmitter 30. If the sound does not match a pre-authorized sound stored in the database (step 108), then the sound is ignored (step 106) and the sound acquisition module 14 continues to listen and pick up environmental noise (returning to step 100). Memory 28 is not permanent memory, allowing the recorded digital signals stored therein to be overwritten, either if they are not matches for signals stored in the database, or if they have already been transmitted to the user.

The controller 24, the memories 26, 28, the transmitter 30 and any other components of module 14, such as a display, interface, or the like, are in communication with one another by any suitable type of data bus, as is well known in the art. Memory 26, 28 may be any suitable type of memory. Buffer memory 36 of filtering earplug 12, to be described in detail below, may similarly be any suitable type of memory capable of storing digital signals. Examples of recording media include a magnetic recording apparatus, an optical disk, a magneto-optical disk, and/or a semiconductor memory (for example, RAM, ROM, flash memory, etc.). Examples of magnetic recording apparatus that may be used in addition to memory 26, 28, 36, or in place of memory 26, 28, 36, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

The filtering earplugs 12 include a housing 22 adapted for insertion into an ear canal of the user. The housing 22 is sized and shaped to completely block out environmental noise from entering the ear canal of ear E. It should be understood that the shape and relative dimensions of housing 22 are shown in FIG. 1 for exemplary purposes only. The housing 22 contains a receiver 34 for receiving the digital signal transmitted by transmitter 30 and antenna 16. An antenna 32 is preferably mounted on housing 22 and is in communication with receiver 34 (or is formed integrally therewith). A converter (e.g., a digital-to-analog converter) for converting the digital signal stored in the buffer memory into an audio signal is disposed in the housing 22. A speaker is in communication with the converter to play the transmitted environmental sound for the user.

The buffer memory 36 is further mounted within housing 22 and is in communication with the receiver 36 for temporarily storing the transmitted digital signal. Conventional audio playback circuitry is further provided for reading the signal stored in buffer memory 36 and playing the signal as audio through speaker 20, which is positioned within the user's ear canal. The audio playback circuitry preferably includes a digital-to-analog amplifier 40, as is conventionally known.

Thus, the housing 22 of earplug(s) 12 completely blocks external noises from being heard by the user. The only sounds heard by the user are delivered via wireless transmission from sound acquisition module 14 to receiver 34 of earplug 12. Only pre-approved sounds, selected by the user and stored in the database recorded in second memory 26, are transmitted and heard by the user.

Figure 5:
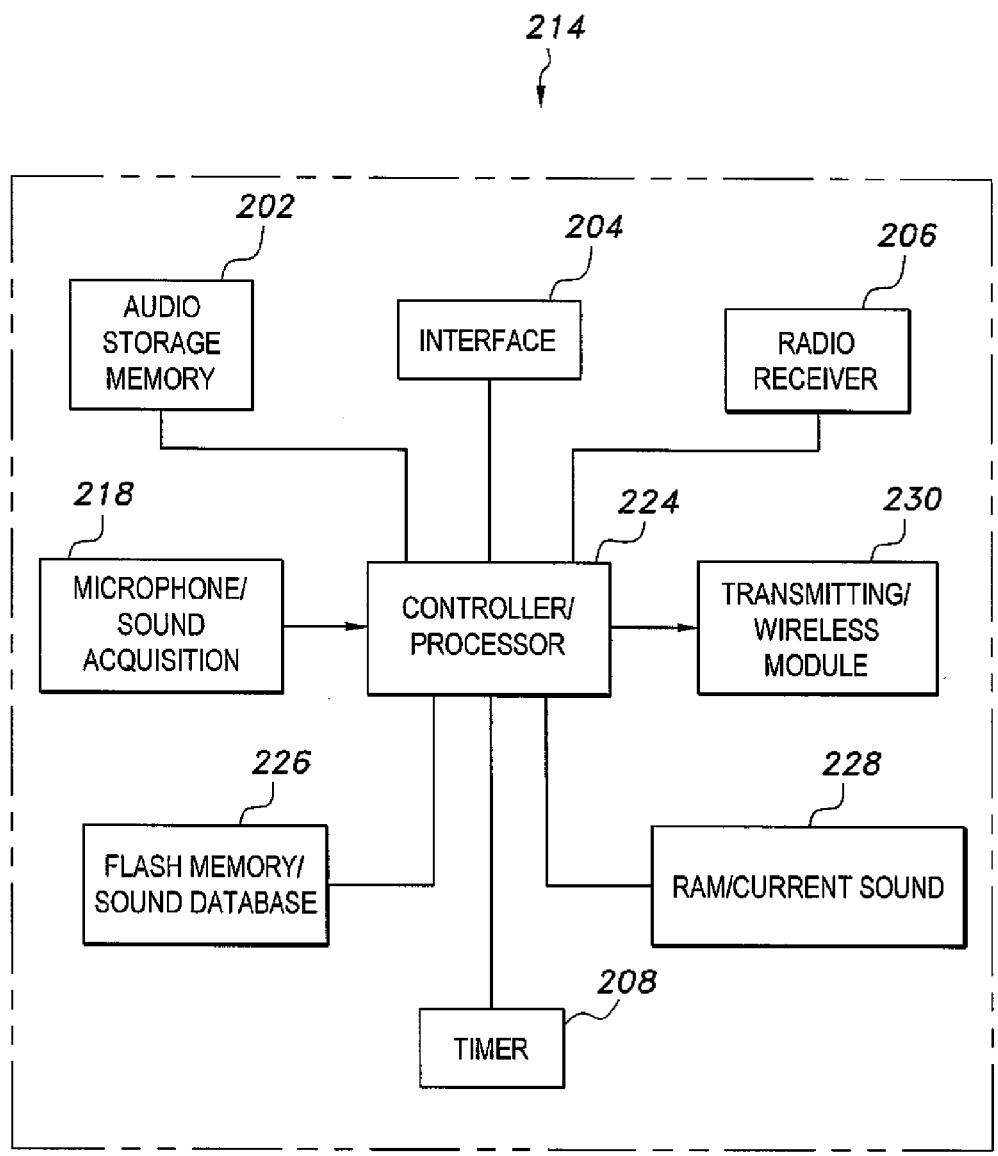
FIG. 5 is a block diagram of the control module circuits for an alternative embodiment of selective filtering earplugs according to the present invention.

In an alternative embodiment, each earplug 12 may be used as an earphone, and the speaker 20 is used to transmit desired audio signals, such as music, audiobooks, AM/FM radio and the like. As shown in FIG. 5, the sound acquisition module 14 of the previous embodiment is now replaced with an audio player 214. Similar to the sound acquisition module 14, the audio player 214 includes a microphone 218 or any other suitable type of acoustic transducer for constantly receiving environmental sounds. The microphone 218 is in communication with a controller 224 such that, when an incoming sound is detected, the received incoming environmental sound is converted to a digital signal (e.g., by an analog-to-digital converter) representing the received environmental sounds.

The controller 224 may be any suitable type of microcontroller, microprocessor, digital signal processor, or the like. The audio player 214 includes an interface 204, which may include a display, such as a touchscreen or the like, allowing the user to control record and playback functions to record and verify sounds in the database. The controller 224 may be associated with, or incorporated into, any suitable type of computing device, for example, a personal computer, a mobile device, a smartphone, a digital audio player or the like.

First memory 228, such as random access memory (RAM) or the like, is provided for storing the digital signal representing the received environmental sounds, and second memory 226, e.g., flash memory, is further provided for storing a database of pre-authorized sound signals. The user selects any desired set of sounds that he or she will permit to be heard, such as the sound of a ringing telephone, a baby crying, a call to prayer or an emergency siren. The user records these pre-authorized sounds with the microphone 218. The controller 224 converts these pre-authorized sounds into digital signals and records them in the database of second memory 226.

The controller 224 compares the digital signal representing the received environmental sounds (stored in first memory 228) with the database of pre-authorized sound signals stored in second memory 226 using digital signal processing algorithms, such as through conventional data vector comparison or the like.

The user may use the audio player 214 as a conventional audio player, allowing the user to listen to digital audio media, such as music, audiobooks or the like, stored in computer readable audio storage memory 202. An interface 204 may be used as in a conventional audio player, allowing the user to select a particular digital audio file to listen to. The retrieved audio is then transmitted to the earplug 12 via a transmitter 230. The earplug 12, as described above, is configured to seal the user's ear canal, thus allowing the user to only hear the desired transmitted audio. The speaker 20 in earplug 12, in the embodiment of FIG. 5, is used to play the transmitted audio file to the user. The transmitter 230 is preferably a wireless transmitter module or assembly.

In use, the speaker 20 acts as a conventional speaker of an earphone or headphone assembly, playing back the desired audio for the user. However, if the digital signal representing the received environmental sounds matches a pre approved sound signal in the database 108, then the processor 224 ceases play of the audio file stored in memory 202 and the transmitter 230 transmits the digital signal representing the selected environmental sound. It should be understood that any suitable type of transmitter may be utilized. Preferably, a wireless antenna is in communication with the transmitter 230.

If the sound does not match a pre-authorized sound stored in the database, then the sound is ignored, and the audio player 214 continues to play back the desired audio files and, simultaneously, listens and picks up environmental noise. Memory 228 is not permanent memory, allowing the recorded digital signals stored therein to be overwritten, either if they are not matches for signals stored in the database, or if they have already been transmitted to the user.

Additionally, a radio receiver 206 may be integrated into the audio player 214, allowing the user to also selectively listen to AM, FM and/or satellite radio transmissions, in addition to the digital audio files stored in audio storage memory 202. Further, a timer 208 may be in communication with the processor 224, allowing the user to further generate an alarm signal at a desired, pre-programmed time. When the pre-programmed time is reached, the processor 224 ceases playback of the desired audio file or radio transmission and, instead, transmits the alarm signal to the user.

It should be understood that the calculations and processing may be performed by any suitable type of computer or control system, such as that diagrammatically illustrated in FIG. 5. Data is entered into controller 214 via any suitable type of user interface 204. Memories 202, 226 and 228 may be any suitable type of computer readable and programmable memory, and may be non-transitory, computer readable storage media. Calculations and processes are performed by processor 224, which may be any suitable type of computer processor and may be displayed to the user on a display of interface 204, which may be any suitable type of display, such as a touchscreen or the like.

The processor 224 may be associated with, or incorporated into, any suitable type of computing device, for example, a personal computer or a programmable logic controller. The interface 204, the processor 224, the memories 202, 226 and 228, along with sound acquisition module 218, transmitter 230, radio receiver 206 and timer 208, and any associated computer readable recording media, are in communication with one another by any suitable type of data bus, as is well known in the art.

Examples of computer-readable recording media include non-transitory storage media, a magnetic recording apparatus, an optical disk, a magneto-optical disk, and/or a semiconductor memory (for example, RAM, ROM, etc.). Examples of magnetic recording apparatus that may be used in addition to memory 202, 226, 228, or in place of memory 202 and/or 226 and/or 228, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

It is to be understood that the present invention is not limited to the embodiments described above, but encompasses any and all embodiments within the scope of the following claims.

I claim:

1. A pair of selective filtering earplugs, comprising:
   an audio player, having:
      a microphone for receiving environmental sounds;
      a circuit for converting the received environmental sounds to a digital signal representing the received environmental sounds;
      a first memory for storing the digital signal representing the received environmental sounds;
      a second memory for storing a database of pre-approved sound signals;
      a digital signal processing circuit for comparing the digital signal representing the received environmental sounds with the database of pre-approved sound signals;
      a third memory for storing digital audio files; and
      a transmitter circuit for selectively transmitting an audio signal representative of a selected one of the digital audio files, wherein transmission of the audio signal representative of the selected one of the digital files is ceased when the received environmental sounds match a pre-approved sound signal in the database, the transmitter circuit transmitting the digital signal representing the received environmental sounds when the received environmental sounds match the pre-approved sound signal in the database;
   a pair of sound-blocking earplugs, at least one of the earplugs being a filtering earplug having:
      a housing adapted for insertion into an ear canal of the user, the housing being sized and shaped to completely block environmental noise;
      a receiver for receiving the audio signal and the digital signal representing the received environmental sounds;
      a circuit for converting the audio signal and the digital signal representing the received environmental sounds into an analog audio signal; and
      a speaker in communication with the converting circuit to play the analog audio for the user.

2. The pair of selective filtering earplugs as recited in claim 1, wherein said circuit for converting the received environmental sounds into the digital signal representing the received environmental sounds includes an analog-to-digital converter.

3. The pair of selective filtering earplugs as recited in claim 2, wherein the transmitter is a wireless transmitter.

4. The pair of selective filtering earplugs as recited in claim 3, wherein the transmitter further comprises a transmitting antenna.

5. The pair of selective filtering earplugs as recited in claim 4, wherein the receiver of the filtering earplug further comprises a receiving antenna.

6. The pair of selective filtering earplugs as recited in claim 5, wherein the filtering earplug further comprises a buffer memory for temporarily storing the received digital signal.

7. The pair of selective filtering earplugs as recited in claim 6, wherein said circuit for converting the digital signal into an audio signal comprises a digital-to-analog converter.

8. The pair of selective filtering earplugs as recited in claim 7, wherein said audio player further comprises a radio receiver.

9. The pair of selective filtering earplugs as recited in claim 8, wherein said audio player further comprises a programmable timer for generating an alarm signal at a desired time.

10. A pair of selective filtering earplugs, comprising:
   an audio player, having:
      a microphone for receiving environmental sounds;
      a circuit for converting the received environmental sounds to a digital signal representing the received environmental sounds;
      a first memory for storing the digital signal representing the received environmental sounds;
      a second memory for storing a database of pre-approved sound signals;

a digital signal processing circuit for comparing the digital signal representing the received environmental sounds with the database of pre-approved sound signals;
a programmable timer for generating an alarm signal at a desired time;
a third memory for storing digital audio files; and
a transmitter circuit for selectively transmitting an audio signal representative of a selected one of the digital audio files, wherein transmission of the audio signal representative of the selected one of the digital files is ceased when the received environmental sounds match a pre-approved sound signal in the database, the transmitter circuit transmitting the digital signal representing the received environmental sounds when the received environmental sounds match the pre-approved sound signal in the database, the transmission of the audio signal representative of the selected one of the digital files further being ceased upon generation of the alarm signal;
a pair of sound-blocking earplugs, at least one of the earplugs being a filtering earplug having:
a housing adapted for insertion into an ear canal of the user, the housing being sized and shaped to completely block environmental noise;
a receiver for receiving the audio signal and the digital signal representing the received environmental sounds;
a circuit for converting the audio signal and the digital signal representing the received environmental sounds into an analog audio signal; and
a speaker in communication with the converting circuit to play the analog audio for the user.

11. The pair of selective filtering earplugs as recited in claim 10, wherein said circuit for converting the received environmental sounds into the digital signal representing the received environmental sounds includes an analog-to-digital converter.

12. The pair of selective filtering earplugs as recited in claim 11, wherein the transmitter is a wireless transmitter.

13. The pair of selective filtering earplugs as recited in claim 12, wherein the transmitter further comprises a transmitting antenna.

14. The pair of selective filtering earplugs as recited in claim 13, wherein the receiver of the filtering earplug further comprises a receiving antenna.

15. The pair of selective filtering earplugs as recited in claim 14, wherein the filtering earplug further comprises a buffer memory for temporarily storing the received digital signal.

16. The pair of selective filtering earplugs as recited in claim 15, wherein said circuit for converting the digital signal into an audio signal comprises a digital-to-analog converter.

17. The pair of selective filtering earplugs as recited in claim 16, wherein said audio player further comprises a radio receiver.

18. A pair of selective filtering earplugs, comprising:
an audio player, having:
a microphone for receiving environmental sounds;
a circuit for converting the received environmental sounds to a digital signal representing the received environmental sounds;
a first memory for storing the digital signal representing the received environmental sounds;
a second memory for storing a database of pre-approved sound signals;
a digital signal processing circuit for comparing the digital signal representing the received environmental sounds with the database of pre-approved sound signals;
a third memory for storing digital audio files; and
a wireless transmitter circuit for selectively wirelessly transmitting an audio signal representative of a selected one of the digital audio files, wherein transmission of the audio signal representative of the selected one of the digital files is ceased when the received environmental sounds match a pre-approved sound signal in the database, the transmitter circuit transmitting the digital signal representing the received environmental sounds when the received environmental sounds match the pre-approved sound signal in the database;
a pair of sound-blocking earplugs, at least one of the earplugs being a filtering earplug having:
a housing adapted for insertion into an ear canal of the user, the housing being sized and shaped to completely block environmental noise;
a wireless receiver for receiving the audio signal and the digital signal representing the received environmental sounds;
a circuit for converting the audio signal and the digital signal representing the received environmental sounds into an analog audio signal; and
a speaker in communication with the converting circuit to play the analog audio for the user.

19. The pair of selective filtering earplugs as recited, in claim 18, wherein said circuit for converting the received environmental sounds into the digital signal representing the received environmental sounds includes an analog-to-digital converter.

20. The pair of selective filtering earplugs as recited in claim 19, wherein the filtering earplug further comprises a buffer memory for temporarily storing the received digital signal.

\* \* \* \* \*